(12) United States Patent
Tsuji et al.

(10) Patent No.: US 7,837,616 B2
(45) Date of Patent: Nov. 23, 2010

(54) ENDOSCOPE, SYSTEM, AND METHOD FOR DETECTING RELATIVE POSITION OF ENDOSCOPE AND MARKERS PLACED AT TARGET AREA

(75) Inventors: Kiyoshi Tsuji, Kunitachi (JP); Akira Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1125 days.

(21) Appl. No.: 11/505,216

(22) Filed: Aug. 16, 2006

(65) Prior Publication Data

US 2006/0276686 A1 Dec. 7, 2006

Related U.S. Application Data

(63) Continuation of application No. PCT/JP2005/002262, filed on Feb. 15, 2005.

(30) Foreign Application Priority Data

Feb. 16, 2004 (JP) ............................. 2004-038856

(51) Int. Cl.
*A61B 1/00* (2006.01)
(52) U.S. Cl. ...................... 600/117; 600/118
(58) Field of Classification Search ................ 600/117, 600/118, 101, 424, 421–423
See application file for complete search history.

(56) References Cited

U.S. PATENT DOCUMENTS

| | | | |
|---|---|---|---|
| 6,115,636 A * | 9/2000 | Ryan ........................... 607/60 |
| 6,332,089 B1 * | 12/2001 | Acker et al. ................ 600/424 |
| 7,447,537 B1 * | 11/2008 | Funda et al. ................ 600/424 |
| 2003/0018246 A1 | 1/2003 | Govari et al. | |
| 2003/0023161 A1 | 1/2003 | Govari et al. | |
| 2003/0055315 A1 | 3/2003 | Gatto et al. | |
| 2003/0085994 A1 | 5/2003 | Fujita et al. | |
| 2007/0149846 A1 * | 6/2007 | Chen et al. .................. 600/117 |

FOREIGN PATENT DOCUMENTS

| | | |
|---|---|---|
| EP | 1 374 792 A1 | 1/2004 |
| JP | 11-099125 | 4/1999 |
| JP | 2002-131009 | 5/2002 |
| JP | 2003-135389 | 5/2003 |
| JP | 2004-041709 | 2/2004 |
| JP | 2004-041724 | 2/2004 |

OTHER PUBLICATIONS

Supplementary Partial European Search Report dated Sep. 16, 2009.
Communication from the European Patent Office dated Aug. 5, 2010.

* cited by examiner

*Primary Examiner*—John P Leubecker
(74) *Attorney, Agent, or Firm*—Scully, Scott, Murphy & Presser, P.C.

(57) ABSTRACT

An objective optical system is provided at a tip end portion of an insertion portion of an endoscope. A plurality of markers capable of transmitting an electromagnetic wave is placed at a target portion in an affected area. Each of the plurality of markers is adapted to transmit at least an information for defining the three-dimensional coordinates of the shape of the target area. At the rear end or the tip end portion of the insertion portion of the endoscope, a sensor is provided for electromagnetically detecting the information defining the three-dimensional coordinates of the shape of the target area and for determining the relative positional relation between the insertion portion and the three-dimensional coordinates of the shape of the target area.

42 Claims, 12 Drawing Sheets

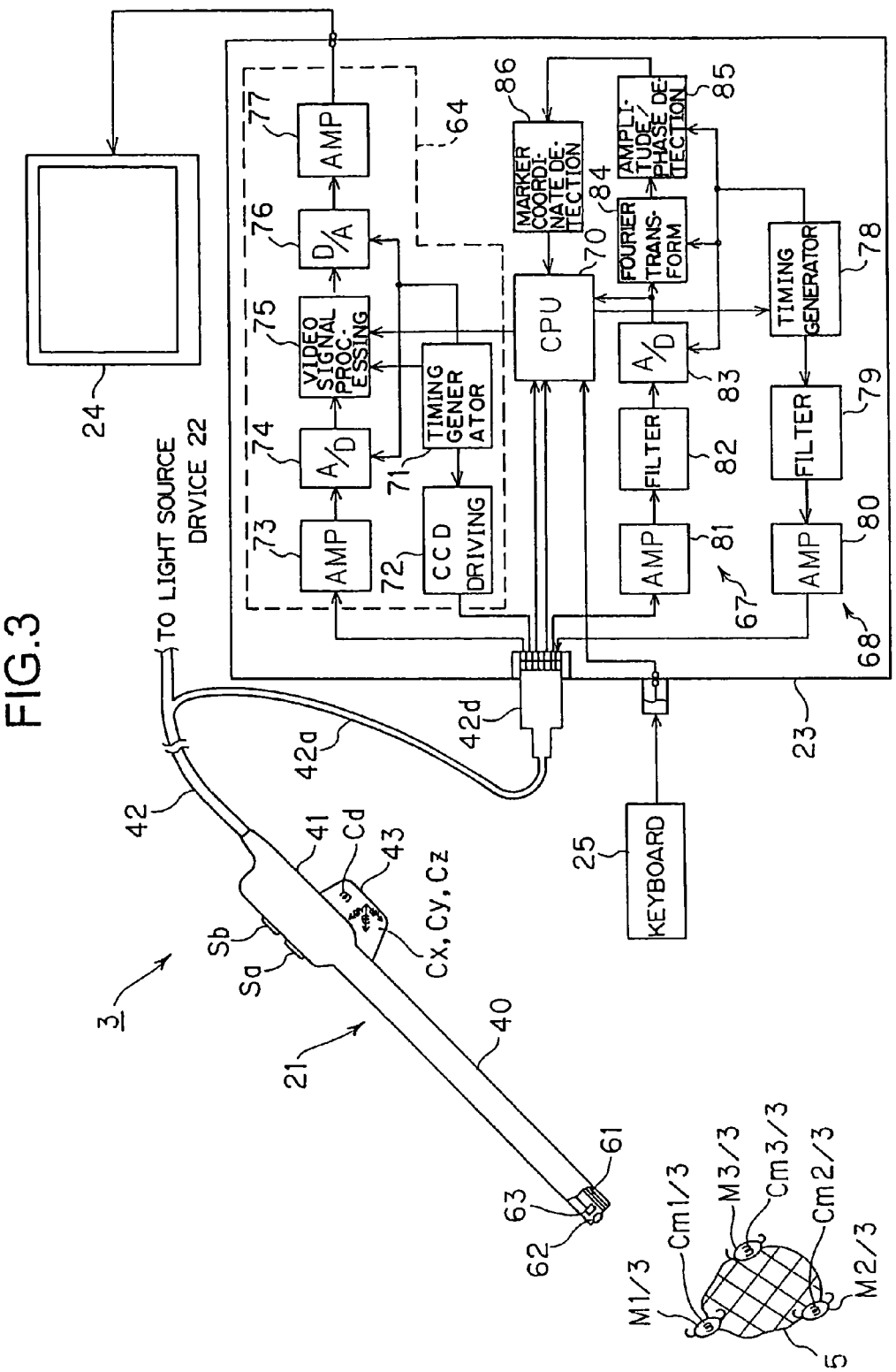

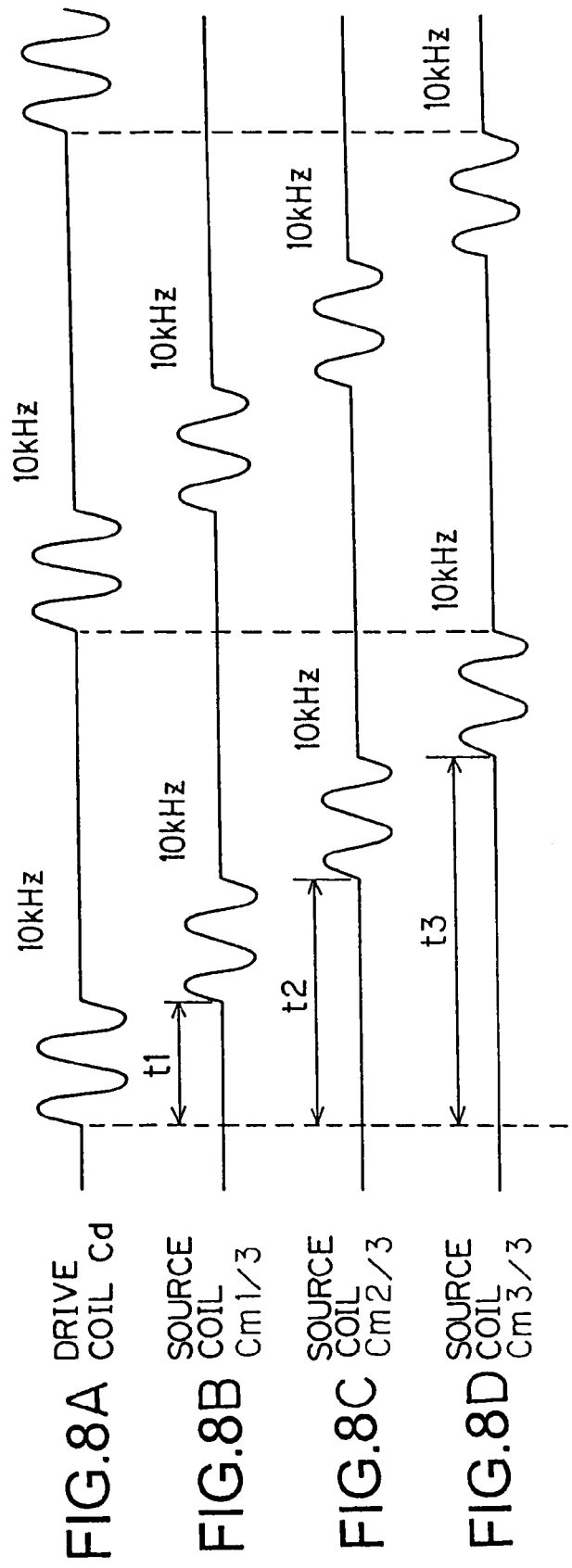

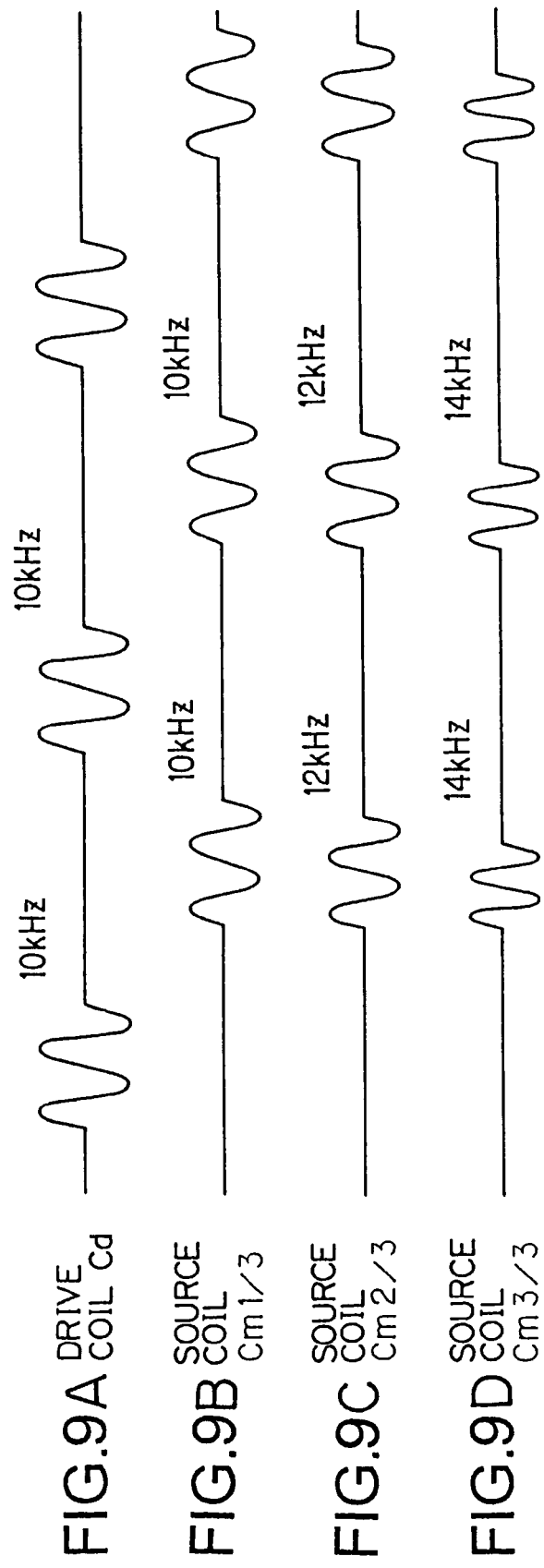

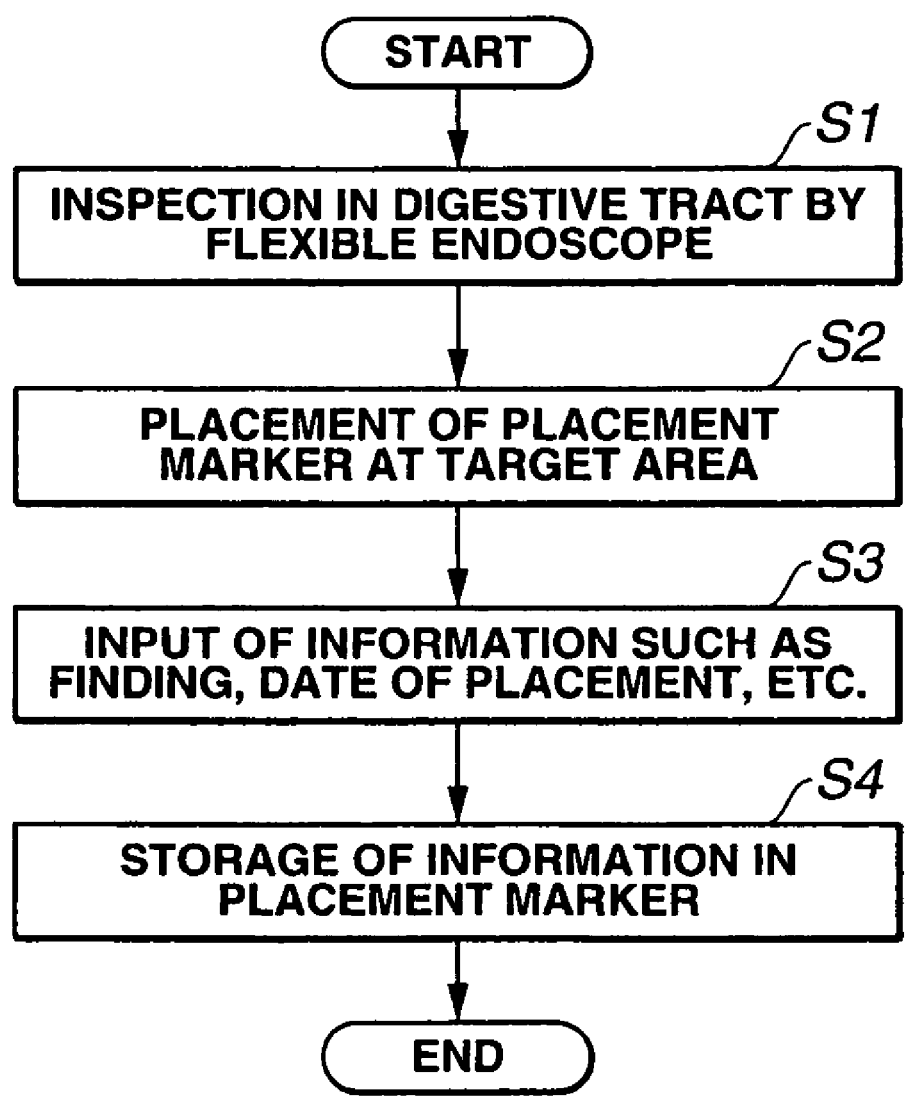

ENDOSCOPE, SYSTEM, AND METHOD FOR DETECTING RELATIVE POSITION OF ENDOSCOPE AND MARKERS PLACED AT TARGET AREA

CROSS REFERENCE TO RELATED APPLICATION

This application is a continuation application of PCT/JP2005/002262 filed on Feb. 15, 2005 and claims benefit of Japanese Application No. 2004-38856 filed in Japan on Feb. 16, 2004, the entire contents of which are incorporated herein by this reference.

BACKGROUND OF THE INVENTION

1. Field of the Invention

The present invention relates to an endoscope to be inserted into a body and the like for endoscopic inspections and treatments and an endoscope system.

2. Description of the Related Art

Recently, an endoscope has been widely employed in the medical field. It is also used for treatment under observation by a flexible endoscope for digestive organs. In this case, a treatment by a surgery under observation by a rigid endoscope can be performed more easily depending on the situation of an affected area and the like.

In such a case in prior examples, an operator places a marker to be a mark at a target portion of the affected area and the like to be inspected/treated in the surgery. Since the position of the marker can not be recognized as an image in optical observation using a rigid endoscope due to intervention of a gastric wall, an intestinal wall and the like, the position is checked by means of sense of feeling from outside the body, X-ray radioscopy and the like in the prior example.

An endoscope device with a construction which can detect the shape of an insertion portion, including the position of the tip end portion of a flexible endoscope, is disclosed in Japanese Unexamined Patent Application Publication No. 2002-131009.

SUMMARY OF THE INVENTION

The present invention is an endoscope provided with an objective optical system at a tip end portion of an insertion portion, comprising a sensor for electromagnetically detecting the position of a marker placed at a target portion and capable of transmission of an electromagnetic wave, provided at a position in a predetermined positional relation with the position of the tip end portion of the insertion portion.

The endoscope system of the present invention comprises:

an endoscope provided with an objective optical system at a tip end portion of an insertion portion;

a marker placed at a target portion and capable of transmission of an electromagnetic wave; and a sensor for detecting the position of the marker, wherein the position of the insertion portion and a positional relation of the marker is detected.

BRIEF DESCRIPTION OF THE DRAWINGS

FIG. 3 is a block diagram showing the entire construction of a second endoscope device;

FIG. 8A to FIG. 8D are diagrams showing timing and the like of a driving waveform by a drive coil and a signal waveform transmitted by the driving from a source coil of the placement marker;

FIG. 9A to FIG. 9D are diagrams showing timing and the like of the driving waveform by the drive coil and a signal waveform transmitted by the driving from the source coil of the placement marker with changed frequency;

FIG. 10 is a flowchart showing a procedure to place a placement marker by endoscopic inspection by a flexible endoscope for digestive organs;

DETAILED DESCRIPTION OF THE PREFERRED EMBODIMENT(S)

Figure 1:
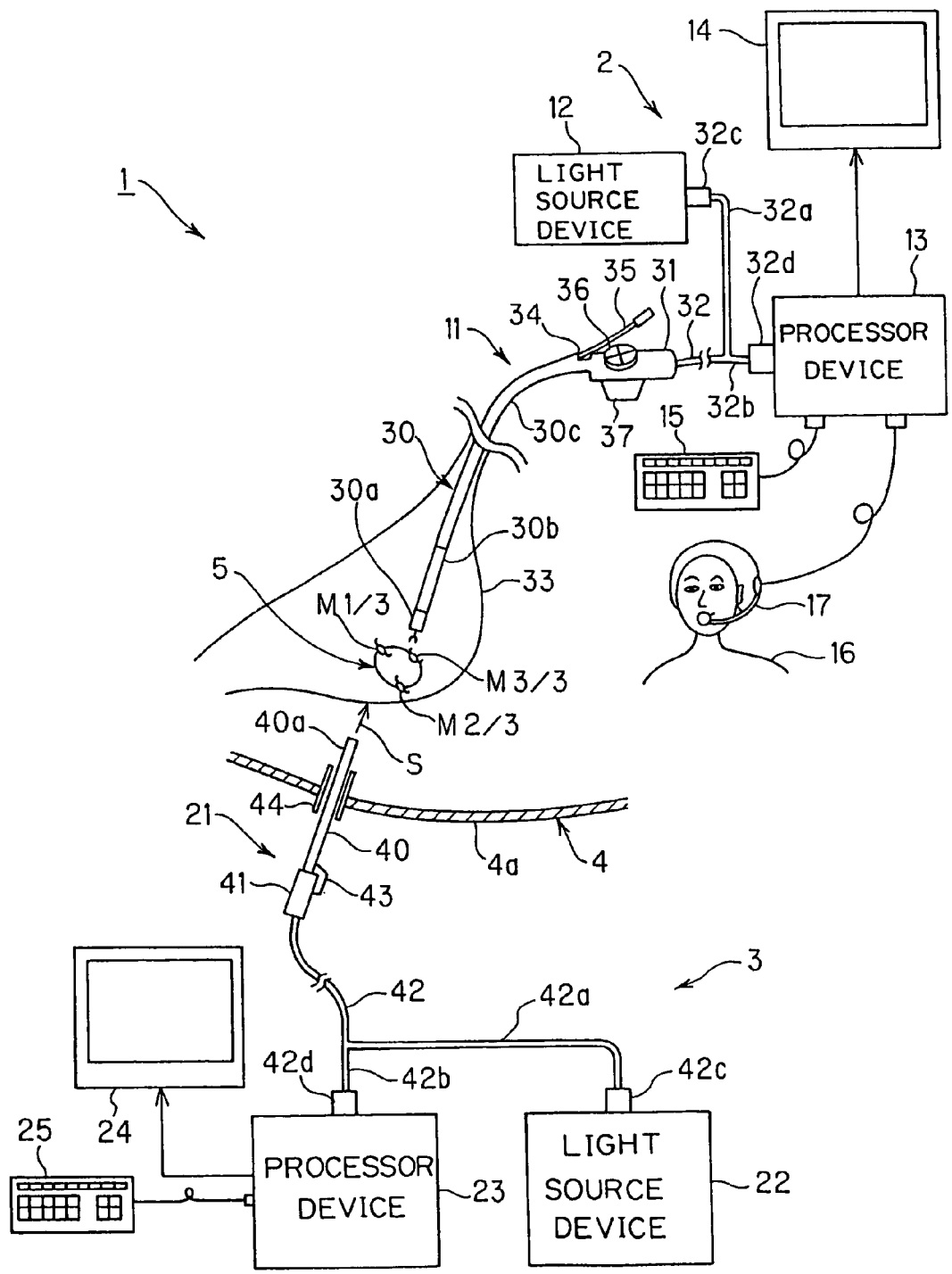
FIG. 1 is a view of an entire construction of an endoscope system provided with an example 1 of the present invention.

Embodiments of the present invention will be explained below by referring to the drawings.

Embodiment 1

An example 1 of the present invention will be described referring to FIGS. 1 to 12.

As shown in FIG. 1, an endoscope system 1 provided with this example comprises a first endoscope device 2 as an endoscope device for digestive organs, for example, a second endoscope device 3 as an endoscope device for surgery, and n pieces of placement (detainment) markers Mi/n (i=1, 2, ... n) including an RF-ID tag and the like placed in a target area (target portion) 5 of a patient 4 to be inspected or treated particularly by the first endoscope device 2 side.

The first endoscope device 2 comprises a flexible endoscope 11 which can be inserted along a curved body cavity, a light source device 12 for supplying illumination light to this flexible endoscope 11, a processor device 13 for executing signal processing for an image pickup element built in the flexible endoscope 11, a monitor 14 for displaying a video signal outputted from this processor device 13, a keyboard 15 connected to the processor device 13 for inputting information to the placement markers Mi/n and the like, and a (mic set provided with a) microphone 17 worn by the head of an operator 16, for example, for enabling input and the like of information by voice to the placement markers Mi/n and the like.

Also, the second endoscope device 3 comprises a rigid endoscope 21 inserted to an abdominal portion 4a of the patient 4, for example, for a surgery, a light source device 22 for supplying illumination light to this rigid endoscope 21, a processor device 23 for executing signal processing for an image pickup element built in the rigid endoscope 21, a monitor 24 for displaying a video signal outputted from this processor device 23, and a keyboard 25 connected to the processor device 23 for input of information.

The flexible endoscope 11 has a flexible and elongated insertion portion 30, a grip portion or handle portion 31 provided at the base end of this insertion portion 30 and gripped by the operator 16, and a universal cable 32 extended from this handle portion 31, and the terminal side of this universal cable 32 is branched to a light guide cable 32a and a signal cable 32b, for example, and each of connectors 32c and 32d provided at the respective ends are detachably connected to the light source device 12 and the processor device 13. This flexible endoscope 11 can be inserted into a gaster 33, for example, via a tract such as a curved esophagus by inserting the insertion portion 30 from a mouth portion.

Also, a treatment instrument insertion port 34 is provided in the vicinity of the base end of the insertion portion 30 so that the treatment instrument can be inserted and its tip end side is protruded through a channel provided in the insertion portion 30 to give treatments or the placement markers Mi/n can be placed using grasping forceps 35, which is a treatment instrument for placement.

Moreover, the insertion portion 30 comprises a rigid tip end portion 30a and a bending portion 30b which can be bent and a flexible portion 30c which is soft (flexible), and the operator 16 can bend the bending portion 30b in an arbitrary vertical or horizontal direction by operating a bending knob 36 provided at the handle portion 31.

Moreover, at the handle portion 31, a driving coil unit 37 for electromagnetically transmitting a signal to write information in the placement markers Mi/n is provided. And as will be described later, the operator performs voice input or the like and transmits on an electromagnetic wave the information to be written from the driving coil in the driving coil unit 37 so that the information transmitted into the memory in the placement markers Mi/n can be written (stored).

On the other hand, the rigid endoscope 21 has a rigid and elongated insertion portion 40, a grip portion or handle portion 41 provided at the base end of this insertion portion 40 and gripped by the operator 16, and a universal cable 42 extended from this handle portion 41. The terminal side of this universal cable 42 is branched to a light guide cable 42a and a signal cable 42b, for example, and each of connectors 42c and 42d provided at the respective ends are detachably connected to the light source device 22 and the processor device 23.

Moreover, at this rigid endoscope 21, a sense coil unit 43 (with a sense coil built in) is mounted in the vicinity of the base end of the insertion portion 40, for example, for detecting the position of the placement marker 6 and capable of detection of a position P of a tip end portion 40a of the insertion portion 40 in this rigid endoscope 21 and its view direction S.

This sense coil unit 43 is also used for detection of the position of placements markers Mi/n. With this rigid endoscope 21, its insertion portion 40 is thrust into a body from the abdominal portion 4a of the patient 4 through a trocar 44.

Figure 2:
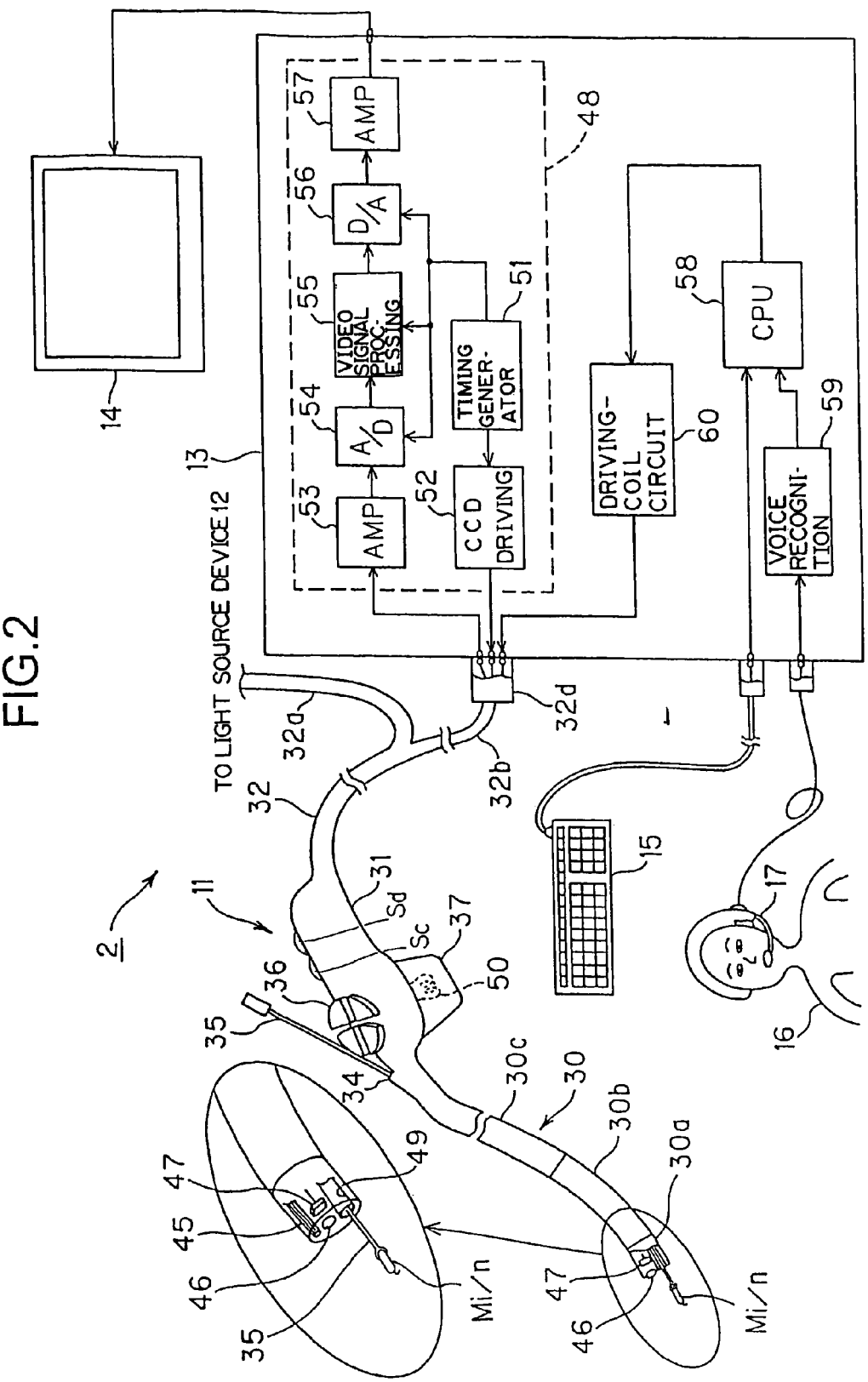
FIG. 2 is a block diagram showing the entire construction of a first endoscope device.

FIG. 2 shows a detailed construction of the first endoscope device 2.

As shown in FIG. 2, a light guide (See enlarged view in FIG. 2) 45 for transmitting illumination light is inserted into the insertion portion 30 of the flexible endoscope 11, and an incident end on its rear end is detachably connected to the light source device 12 shown in FIG. 1. And the illumination light supplied from the light source device 12 is transmitted and outputted from an output surface at the tip end of the light guide 45. The output surface of the light guide 45 is mounted at an illumination window of the tip end portion 30a.

At the tip end portion 30a, an observation window is provided adjacently to the illumination window, an objective lens 46 is mounted at this observation window, and a charge-coupled device (abbreviated as CCD) 47, for example, is arranged as an image pickup device at its image forming position. This CCD 47 is electrically connected to a contact of the connector 32d by a signal line. And when the user connects this connector 32d to the processor device 13, it is connected to a driving & signal processing circuit 48 in the processor device 13.

Also, a channel 49 is provided in the insertion portion 30, through which the treatment instrument such as the grasping forceps 35 and the like for placement of the placement markers Mi/n can be inserted.

Moreover, a driving coil 50 for transmitting information to be written in the placement markers Mi/n by the electromagnetic wave is accommodated in the driving coil unit 37 provided at the handle portion 31. This driving coil 50 is connected to a signal line inserted in the handle portion 31 and the universal cable 32 and connected to the processor device 13 through the connector 32d.

The driving & signal processing circuit 48 built in the processor device 13 has a timing generator 51 for generating a timing signal such as various clocks and a CCD driving circuit 52 for generating a CCD driving signal for driving the CCD 47 in synchronization with the timing signal.

Also, the circuit has an amplifier 53 for amplifying a CCD output signal outputted from the CCD 47 upon application of the CCD driving signal, an A/D converter 54 for A/D converting the output signal from this amplifier 53, a video signal processing circuit 55 for signal processing of video signal generation to the digital CCD output signal outputted from this A/D converter 54, a D/A converter 56 for D/A converting the video signal outputted from this video signal processing circuit 55 and an amplifier 57 for amplifying an analog video signal outputted from this D/A converter 56.

The analog video signal amplified by this amplifier 57 is inputted to the monitor 14 and an endoscopic image corresponding to this video signal is displayed on the display surface of the monitor 14.

The timing generator 51 also supplies the timing signal to the A/D converter 54, the video signal processing circuit 55 and the D/A converter 56.

Moreover, in this processor device 13, a CPU 58 for control processing, a voice recognition circuit 59 for voice recognition and a driving-coil driving circuit 60 for generating a signal for driving the driving coil 50 are incorporated.

To the CPU 58, data and the like is inputted by operation of the keyboard 15 by the operator 16 and the like. Also, a voice signal inputted by the operator 16 and the like through the mic set 17 is voice-recognized by the voice recognition circuit 59, converted to corresponding character information and inputted to the CPU 58.

The CPU 58 outputs a signal corresponding to data and character information inputted from the keyboard 15 and the voice recognition circuit 59 to the driving-coil driving circuit

60. The driving-coil driving circuit 60 transmits a signal corresponding to the inputted data and character information to the driving coil 50 in the handle portion 31, and this driving coil 50 changes this inputted information from the CPU 58 side to a modulated signal and emits it as an electromagnetic wave.

Figure 5:
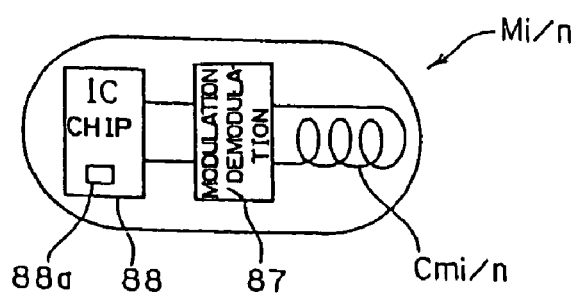
FIG. 5 is a view showing an outline construction of a placement marker.

The placement marker Mi/n receives this electromagnetic wave and uses a part thereof as a power source and also demodulates and stores the transmitted information in a built-in memory 88a (See FIG. 5).

Specifically, in a signal emitted from the driving coil 50 as the electromagnetic wave, finding by the operator 16, date of placement (of the placement markers 6), serial number (of the placement markers Mi/n) (that is, 1/n, 2/n, . . . n/n) and the like are superimposed. And the electromagnetic wave is received by the source coil Cmi built in the placement marker Mi/n for transmission and receiving. Moreover, a part of it is further used as a power source, and the transmitted signal is demodulated to generate a signal corresponding to the above input information and the signal is stored in the memory 88a of an IC chip 88 in the placement marker Mi/n.

In this preferred embodiment, other than the position information by the signal transmitted from the source coil Cmi of the placement marker Mi/n, information stored in the memory 88a of the placement marker Mi/n is read out so that the subsequent treatment by the rigid endoscope 21 side can be performed more smoothly.

The position to provide the driving coil 50 is not limited to the provision at the handle portion 31 of the flexible endoscope 11, but it may be provided at another position or a position other than the flexible endoscope 11, at the processor device 13, for example.

FIG. 3 shows a detailed construction of the second endoscope device 3. Also, FIG. 4A shows details of the rigid endoscope 21 constituting the second endoscope device 3.

Figure 4A:
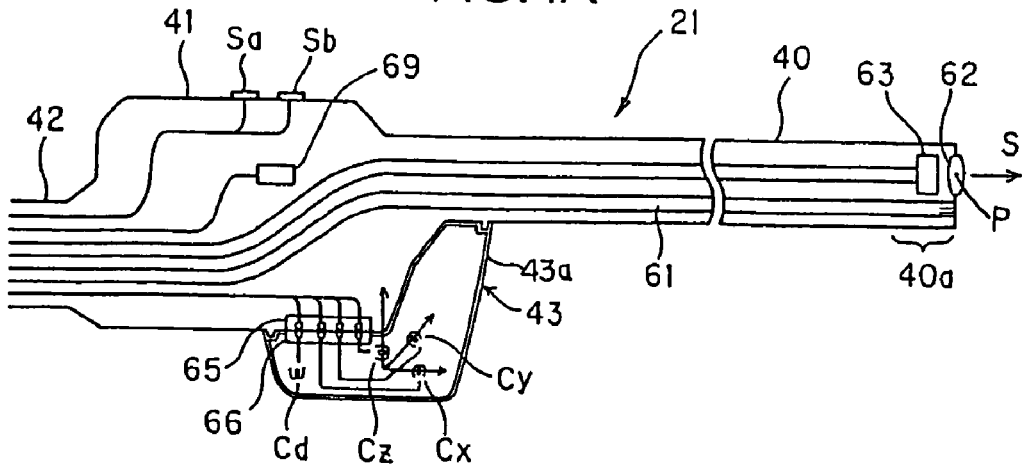
FIG. 4A is a view showing an internal construction of a rigid endoscope.

As shown in FIG. 4A, a light guide 61 is inserted into the rigid insertion portion 40 of the rigid endoscope 21, and this light guide 61 is further inserted into the universal cable 42 extended from the handle portion 41.

And as shown in FIG. 1, when the user connects the connector 42a to the light source device 22, the illumination light incident from the light source device 22 via the connector 42a is transmitted by the light guide 61. The output surface at the tip end of this light guide 61 is mounted to an illumination window of the tip end portion 40a of the insertion portion 40, and the transmitted illumination light is outputted forward from this illumination window.

Moreover, at an observation window provided adjacently to the illumination window, an objective lens 62 is mounted at this observation window, and a CCD device 63 is arranged at its image forming position. This CCD 63 is connected to a driving & signal processing circuit 64 built in the processor device 23 through a signal line inserted into the insertion portion 40 and the like as shown in FIG. 3.

As shown in FIG. 4A, the sense coil unit 43 is detachably equipped at the handle portion 41 of this rigid endoscope 21.

For example, at one location on the outer circumferential surface of the handle portion 41, a connector receiver 65 is provided, and to this connector receiver, a connector 66 provided at a case 43a on the sense coil unit 43 side is detachably connected. A projection portion is provided on the outer circumferential face of the handle portion 41, and the case 43a is fitted with this projection portion and detachably mounted.

In the case 43a of this sense coil unit 43, sense coils Cx, Cy, Cz and a drive coil Cd are built in, and the sense coils Cx, Cy, Cz and the drive coil Cd are connected to a contact of the connector 66 by a lead wire.

And these sense coils Cx, Cy, Cz and the drive coil Cd are connected to a sense-coil processing circuit 67 and a drive-coil signal processing circuit 68 in the processor device 23 shown in FIG. 3, respectively, by a signal line connected to a contact of the connector receiver 65.

It is to be noted that one of the sense coils Cx, Cy, Cz may act as the drive coil Cd.

Figure 4B:
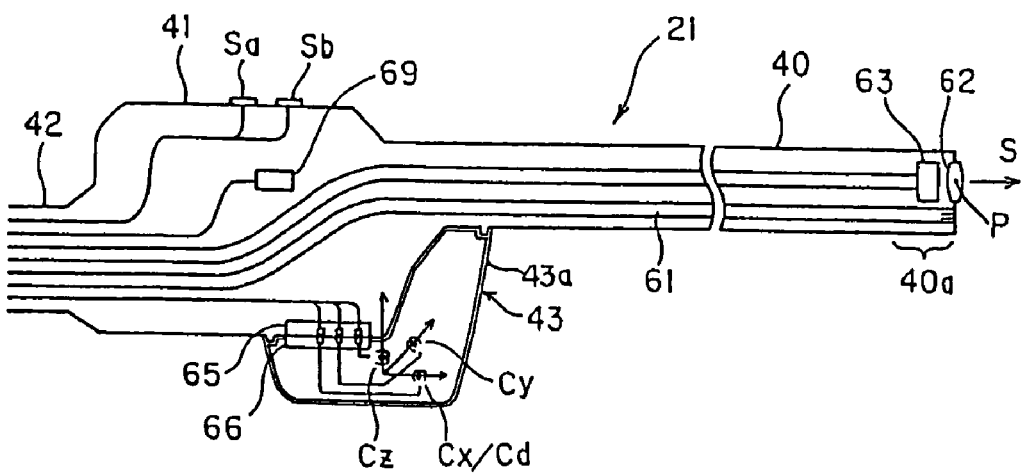
FIG. 4B is a view showing an internal construction of a rigid endoscope of a variation.

FIG. 4B shows a construction of a variation in which the sense coil Cx acts also as the drive coil Cd. In FIG. 4B, the sense coil Cx/Cd is used as the sense coil Cx and also as the drive coil Cd. Therefore, in this case, the drive coil Cd can be omitted.

Also, in this preferred embodiment, since the sense coil unit 43 is detachable in the rigid endoscope 21, a memory IC 69, for example, in which a scope ID specific to the rigid endoscope 21 is written, is built in the respective rigid endoscopes 21 so that the sense coil unit 43 can be used in the state suited for the rigid endoscope 21 to which it is actually mounted, as shown in FIG. 4A.

And the information of this memory IC 69 is read by a CPU 70 provided in the processor device 23, and the information is used at a treatment when the tip end portion 40a of the rigid endoscope 21 is brought close to a portion where the placement markers Mi/n are placed.

If the sense coil unit 43 is detachable as in the above, when the mechanical dimensions including a length of the insertion portion 40 of the rigid endoscope 21 are different, a relative position between the positions of the sense coils Cx, Cy, Cz and the position P of the tip end portion 40a of the insertion portion 40 differs, and to determine the positional relation between them, information which can uniquely determine the relation is required.

If the sense coil unit 43 is made detachable to have compatibility to be combined detachably with various rigid endoscopes in this way, the above information for the individual rigid information is required. In order to achieve this, in this preferred embodiment, information specific to the individual rigid endoscopes is stored in the memory IC 69 in the respective rigid endoscopes 21 in addition to the scope ID, and the information is read by the processor device 23 side and converted to required information and then, used at position detection by the sense coil unit 43 as well as position detection of the tip end portion 40a.

Figure 6:
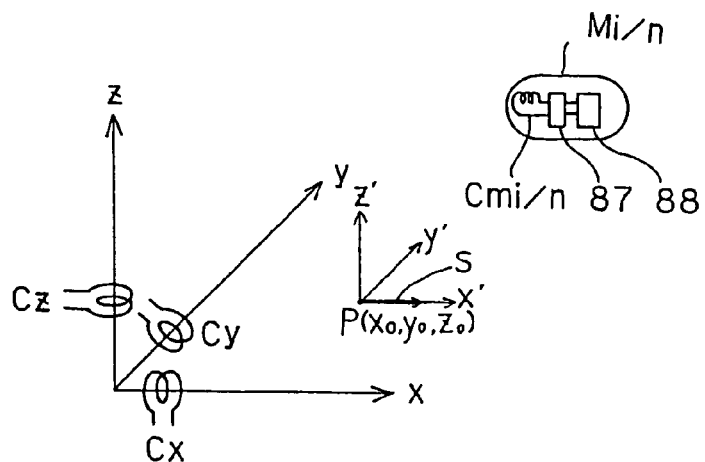
FIG. 6 is a view showing a state of position detection and the like of a sense coil and the placement marker as well as the tip end portion.

In FIG. 6, which will be described later, a state is shown where the position P of the tip end portion 40a and the like is displayed in the coordinate of position detection of the placement markers Mi/n by the sense coils Cx, Cy, Cz.

In this case, the information specific to the rigid endoscope includes information on the positions of the sense coils Cx, Cy, Cz by mounting of the sense coil unit 43 and the mechanical dimensions of the rigid endoscope 21 (length of the insertion portion 40, a distance from the positions of the sense coils Cx, Cy, Cz to the objective lens 62 of the tip end portions 40a and the space coordinate position) as well as information on a lens magnifying power of the objective lens 62, a lens viewing angle, a direction of oblique view (oblique viewing angle) of a straight viewing type and an oblique viewing type, etc.

All the information may be stored in the above memory IC 69 or only the model number and product number are stored in the rigid endoscope 21 and they may be converted one-to-one by an LUT (look UP table) memory, not shown, which is provided on the processor device 23 side for use. Identifying means of the rigid endoscope 21 is not limited to the memory IC 69 storing the scope ID but identification can be similarly achieved by optical reading means and the like such as a barcode.

Also, the handle portion 41 of the rigid endoscope 21, for example, is provided with switches Sa, Sb for instruction operation as shown in FIG. 4A. And when the switch Sa is pressed to be turned on, its operation signal is inputted to the CPU 70 provided in the processor device 23.

And upon receipt of this instruction signal, the CPU 70 transmits a signal from the drive coil Cd to the placement markers Mi/n, and the placement markers Mi/n start transmission operation upon receipt of this signal.

Also, by operating the switch Sb, the drive coil Cd transmits a signal to stop transmission to the placement markers Mi/n, and the placement markers Mi/n stop transmission. Control can be made in this way so that a signal is not emitted unnecessarily.

It is to be noted that the switches Sa, Sb may be provided at the sense coil unit 43. In this case, the signal is transferred to the CPU 70 through the connector 66 and the connector receiver 65.

Alternatively, the switch Sa may have both functions of transmission start and transmission stop.

The driving & signal processing circuit 64 in the processor device 23 shown in FIG. 3 has the same construction as the driving & signal processing circuit 48 shown in FIG. 2.

That is, the driving & signal processing circuit 64 has a timing generator for generating various timing signals and a CCD driving circuit 72 for generating a CCD driving signal for driving the CCD 63 in synchronization with the timing signal.

Also, the circuit has an amplifier 73 for amplifying a CCD output signal outputted from the CCD 63 upon application of the CCD driving signal, an A/D converter 74 for A/D converting the output signal from this amplifier 73, a video signal processing circuit 75 for signal processing of video signal generation with respect to the digital CCD output signal outputted from this A/D converter 74, a D/A converter 76 for D/A converting the video signal outputted from this video signal processing circuit 75 and an amplifier 77 for amplifying an analog video signal outputted from this D/A converter 76.

The analog video signal amplified by this amplifier 77 is inputted to the monitor 24 and an endoscopic image corresponding to this video signal is displayed on the display surface of the monitor 24.

The timing generator 71 also supplies the timing signal to the A/D converter 74, the video signal processing circuit 75 and the D/A converter 76.

Moreover, the drive-coil signal processing circuit 68 has a timing generator (clock generator) 78 for generating a clock of various timing clocks, a filter 79 by BPF set so that the clock from this timing generator 78 is passed, and an amplifier 80 for amplifying the clock having passed this filter 79.

The clock outputted from the timing generator 78 to the filter 79 side is controlled by the CPU 70. That is, upon turning-on of the switch Sa, the CPU 70 outputs a clock from the timing generator 78 to the filter 79 side.

The clock with a predetermined frequency amplified via the amplifier 80 is applied to the drive coil Cd. This drive coil Cd emits a signal of the applied clock as an electromagnetic wave, and this electromagnetic wave is received by the source coil Cmi of the placement marker Mi/n and used as a power source. Also, by the supply of the power source, a signal used for position detection and the like is transmitted.

The signal transmitted from the placement marker Mi/n side is received by the sense coils Cx, Cy, Cz and inputted in an amplifier 81 in the sense-coil processing circuit 67 in the processor device 23. After the signal is amplified by this amplifier 81, a signal in a predetermined bandwidth is extracted by a filter 82 and A/D converted by an A/D converter 83 to a digital signal.

A Fourier transform circuit 84 conducts frequency analysis to extract the inputted signal, specifically, a frequency component of the signal transmitted from the source coil of the placement marker Mi/n and extracts the frequency component of the signal from the frequency analysis result.

The extracted signal is outputted to an amplitude/phase detection circuit 85, and the amplitude/phase detection circuit 85 detects an amplitude value and a phase value (shifting from the reference phase) of the signal and outputs them to a marker coordinate detection circuit 86. The marker coordinate detection circuit 86 detects (calculates) a three-dimensional coordinate of the respective placement markers Mi/n from the amplitude and phase values of the signal detected by the three sense coils Cx, Cy, Cz.

The calculated information is outputted to the video signal processing circuit 75 through the CPU 70 and superimposed and the like on the video signal of the endoscopic image generated by the video signal processing circuit 75 so that the position of the placement markers M/n can be displayed together with the endoscopic image on the display screen of the monitor 24.

Moreover, the CPU 70 to which the output signal from the A/D converter 83 is inputted decodes the modulated (superimposed) information to a signal for position detection and obtains information written in the memory 88a of the IC chip 88. And the CPU 70 performs control processing of output to the video signal processing circuit 75 so that the information such as written finding and so on can be displayed together with the position of the placement markers Mi/n on the display screen of the monitor 24.

FIG. 5 shows the construction of the placement marker Mi/n.

The placement marker Mi/n comprises the source coil Cmi/n used for transmitting and receiving, a modulation/demodulation circuit 87 connected to this source coil Cmi/n for modulation/demodulation and the IC chip 88 having the memory 88a for storing transmitted information for writing/reading and the like to/from the memory 88a in an exterior case in the capsule shape, for example.

In this preferred embodiment, information for later treatment by the flexible endoscope 11 is transmitted and written (stored) in the memory 88a.

And at treatment by the rigid endoscope 21, the IC chip 88 is driven for transmission for position detection and also reads, modulates and transmits the information stored in the memory 88a. And on the rigid endoscope 21 side, the transmitted signal is received and used for smooth or appropriate treatment by referring to the finding in the demodulated information, for example.

FIG. 6 shows a state where the placement marker Mi/n is detected by the sense coils Cx, Cy, Cz.

With regard to the sense coils Cx, Cy, Cz, an uniaxial coil (solenoid coil) is arranged with a sensitivity (that is, directivity) in three orthogonal axes of x, y, z directions and used for detecting intensity of an electromagnetic field and phase shifting from the source coil Cmi/n of the placement marker Mi/n, and the three-dimensional coordinate position of the source coil Cmi/n is calculated from the detection information.

Also, the position of the tip end portion 40a (or the objective lens 62 in the tip end portion 40a) of the insertion portion 40 to be the predetermined three-dimensional coordinate position with the origin set at the sense coils Cx, Cy, Cz can be calculated from information from the IC memory 69.

In FIG. 6, with the origin at the sense coils Cx, Cy, Cz, the coordinate of the position P of the tip end portion 40a is shown by (x0, y0, z0). In this preferred embodiment, the three-dimensional coordinate position of the source coil Cmi/3 can be displayed with the origin at the position of the tip end portion 40a, for example. In this case, when it is shown in FIG. 6, with respect to the eye position of the objective lens 62 set as the position P of the tip end portion 40a, the coordinate system is shown by (x', y', z') with the origin at the position P.

Moreover, in this preferred embodiment, by arranging the sense coil Cx so that it has a directivity in the axial direction of the insertion portion 40, the view direction S of the objective lens 62 is set in parallel with the x-axis direction in the coordinate system (x, y, z) with the origin at the sense coils Cx, Cy, Cz and it is also set in the x' direction in the coordinate system (x', y', z') with the origin at the position P of the tip end portion 40a. Therefore, mutual conversion is made possible between the coordinate system with the origin at the sense coils Cx, Cy, Cz and the coordinate system with the origin at the position P of the tip end portion 40a. In this preferred embodiment, the case of the straight view type is shown.

Figure 7A:
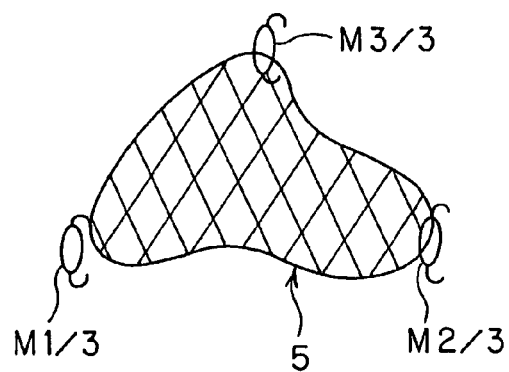
FIG. 7A is a view showing an example to set placement markers according to the shape of the target portion.
Figure 7B:
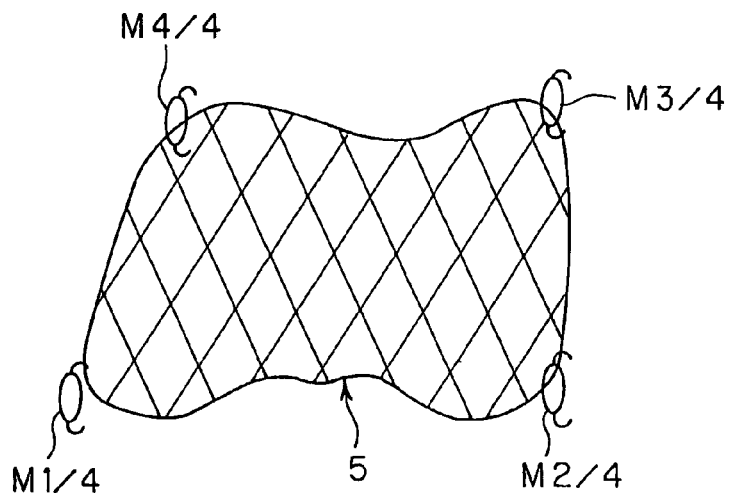
FIG. 7B is a view showing an example to set placement markers according to the shape of the target portion.

FIGS. 7A and 7B show a state where the placement markers Mi/n are placed with respect to the target area 5 to be focused such as an affected area.

It is preferable that the placement markers Mi/n are placed as in FIG. 7A or FIG. 7B according to the shape of the target area 5 of the affected area and the like.

If the target area 5 is in the shape close to a substantial triangle as shown in FIG. 7A, it is preferable to place three placement markers M1/3, M2/3, M3/3 at positions close to each apex.

Alternatively, if the target area 5 is in the shape close to a substantial square as shown in FIG. 7B, it is preferable to place four placement markers M1/4, M2/4, M3/4, M4/4 at positions close to each apex.

If the target area 5 is a circle or an oval, three or more placement markers Mi/n may be placed along its outer shape.

It becomes important that the total number n of the placement markers Mi/n and the serial number i/n can be recognized to avoid omission of maneuver at a surgery.

FIG. 8A to FIG. 8D show a timing of a signal transmitted from the drive coil Cd of the rigid endoscope 21 to the placed three placement markers Mi/3, for example, and a signal to be transmitted for position detection and the like by the source coil Cmi on the placement markers Mi/3 side.

As shown in FIG. 8A, the drive coil Cd outputs a burst waveform with an oscillation frequency of 10 KHz, for example, as a signal of a predetermined cycle.

Upon receipt of it, power is supplied to the placement markers M1/3 to M3/3, which transmit output signals shown in FIGS. 8B to 8D, respectively.

The signals shown in FIGS. 8B to 8D are fundamental waves (carrier waves) of the respective output signals. In this fundamental wave, specific information recorded in the memory 88a in the respective placement markers M1/3 to M/3/and information on finding and the like are superimposed.

In this preferred embodiment, it is necessary to recognize the position information of the three placement markers M1/3 to M3/3, and the output signals of the three placement markers M1/3 to M3/3 are, as shown in FIGS. 8B to 8D, are transmitted at a transmission timing of the burst waveform of the drive coil Cd at each time t1, t2, t3 with a predetermined amplitude so that it can be known which signal corresponds to which source coil Cmi/3 when the signals are received by the sense coils Cx, Cy, Cz provided at the rigid endoscope 21 for surgery.

Moreover, by detecting a time lag from the time t1, t2, t3 as a phase shifting of the signal waveform from the source coil Cmi/3, a distance between the sense coils Cx, Cy, Cz to the respective source coil Cmi/3 can be detected. Also, from the above distance, directivity of the sense coils Cx, Cy, Cz and the amplitude values of the signal waveforms, a position of the source coil Cmi/3 in the three-dimensional coordinate can be calculated with the origin in the coordinate system of the sense coils Cx, Cy, Cz, for example.

Also, with the origin at the position of the tip end portion 40a (or the objective lens 62 in the tip end portion 40a) of the insertion portion 40 to be the predetermined three-dimensional coordinate position if the origin is set at the sense coils Cx, Cy, Cz, the position of the source coil Cmi/3 in the three-dimensional coordinate can be calculated.

In this preferred embodiment, in order to facilitate visual approach of the tip end portion 40a of the rigid endoscope 21 to the target area 5 where the placement markers Mi/3 are placed, when the calculated result of the position of the source coil Cmi/3 in the three-dimensional coordinate is displayed, the tip end portion 40a of the insertion portion 40 is displayed as the origin of the three-dimensional coordinate system.

This is made possible, at placement of the placement markers M1/3 to M3/3 by maneuver using the endoscope, since serial number data is also inputted when predetermined information is inputted from the endoscope device 2 side for digestive organ to the respective placement markers Mi/3, information that "a transmission signal is outputted at each time t1, t2, t3 after receiving of the burst waveform from the drive coil Cd" is also programmed.

FIG. 9A to FIG. 9D show another transmission method different from that in FIG. 8A to FIG. 8D.

As shown in FIG. 9A, the transmission frequency is set to the burst waveform of 10 kHz, for example.

Upon receiving it, power is supplied to the source coils Cm1/3 to Cm3/3 built in the placement markers M1/3 to M3/3, and each of them transmits an output signal shown in FIGS. 9B to 9D, respectively. All the transmission signals from these source coils Cm1/3 to Cm3/3 have the same start timing but their transmission frequencies are different from each other such as 10 kHz, 12 kHz, 14 kHz, respectively.

In this case, too, it is necessary to recognize the position information of the three placement markers M1/3 to M3/3, but since the source coils Cm1/3 to Cm3/3 are transmitted with different frequencies such as 10 kHz, 12 kHz, 14 kHz, respectively, by receiving them by the sense coils Cx, Cy, Cz provided in the rigid endoscope 21 for surgery, which source coil Cmi it corresponds to can be recognized by the frequency.

This is made possible, at placement of the placement markers M1/3 to M3/3, since the serial number data is also inputted when predetermined information is inputted from the endoscope device 2 side for digestive organ to the respective placement markers Mi/3, information that "when a burst waveform is received from the drive coil Cd, fundamental waves of 10 kHz, 12 kHz, 14 kHz should be outputted, respectively" is also programmed.

Moreover, FIGS. 9B to 9D show fundamental waves of the output signals. In this fundamental wave, the specific information recorded in the memory 88a in the respective placement markers Mi/3 and the like is superimposed. Alternatively, the timing to transmit on the fundamental wave and the timing to transmit with specific information superimposed may be changed alternately in a certain cycle.

A procedure of diagnosis by the flexible endoscope 11 for digestive organs for a treatment target area such as an affected area using the endoscope system 1 with this construction, placement of the placement markers Mi/n based on the diagnosis results and a surgery by the rigid endoscope 21 using the so placed placement markers Mi/n will be described referring to FIGS. 10 and 11.

As shown in FIG. 10, at the first Step S1, endoscopic inspection is conducted by the flexible endoscope 11 for digestive organs.

Specifically, as shown in FIG. 1, for example, the flexible endoscope 11 for digestive organs is inserted from the mouth portion of the patient 4 to conduct the endoscopic inspection of the inside of the digestive organ, a gaster 33, for example.

Based on this endoscopic inspection, a treatment by this flexible endoscope 11, endoscopic mucosal resection (EMR) or the like, for example, as a mucous membrane ablative surgery under observation by endoscope is performed.

And if a surgery by a rigid endoscope is more preferable for treatment of the target area 5, the operator 16 places the placement markers Mi/n at the treatment target area 5 as shown in Step S2. At placement of the placement markers Mi/n, three or more placement markers Mi/n are placed surrounding the target area 5 by using the grasping forceps 35 and the like inserted into the channel 49 of the flexible endoscope 11.

At placement of the placement markers Mi/n, by employing the grasping forceps 35 provided with the placement marker Mi/n with the outer diameter smaller than the inner diameter of the channel 49 and a grip portion capable of being inserted into the channel 49 at the tip end, pain is not forced for the patient 4, or the operator 16 can accomplish easy placement, as shown the enlarged view in FIG. 2.

Moreover, at placement of the placement markers Mi/n, by mounting a hook or the like at the placement marker Mi/n in advance and by inserting the tip end of the hook into the surface of the target area 5 in an affected area or the like, the placement marker Mi/n can be placed. Also, placement can be achieved without using a hook but by using bio-adhesive polymer applied on the outer surface of the placement marker Mi/n.

And the operator 16 inputs, as shown in Step S3, findings, date and time of placement, serial numbers with respect to the total number n of the placement markers Mi/n to be placed and the like by voice input or the like through the mic set 17, for example.

After the input, by transmission or voice input of writing or the like to the placement markers Mi/n, the CPU 58 in the processor device 13 operates the driving-coil driving circuit 60 so that inputted information is transmitted from the driving coil 50.

And as shown in Step S4, the placement marker Mi/n receives the signal by the source coil Cmi/n and uses it as power source and stores the transmitted information in the memory 88a in the IC chip 88.

After that, the operator 16 pulls the flexible endoscope 11 out of the body cavity.

And at an appropriate time and date after the time and date of the placement, the operator will conduct a surgery using the rigid endoscope 21. A typical treatment procedure for that case is shown in FIG. 11.

As shown in Step S11, the insertion portion 40 of the rigid endoscope 21 is thrust from the abdominal portion 4a or the like of the patient 4 through the trocar 44.

And the endoscopic image captured by the CCD 63 of this rigid endoscope 21 is displayed on the monitor 24.

Figure 11:
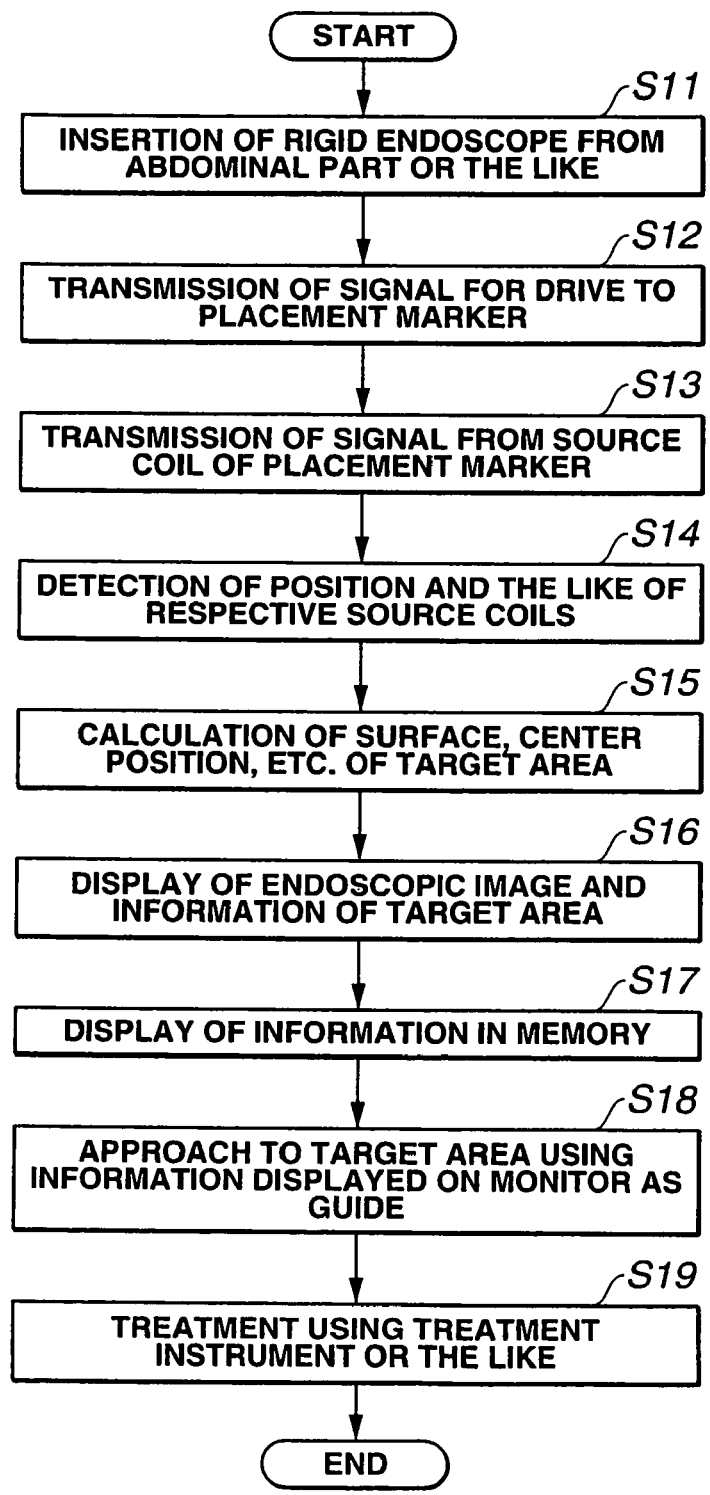
FIG. 11 is a flowchart showing a procedure of a surgery by a rigid endoscope after placing the placement marker by a flexible endoscope for digestive organs.

The processing from Step S12 to Step S17 in FIG. 11 may be performed under control of the CPU 70 according to a program 70a built in the CPU 70.

The operator operates the switch Sa or the like to transmit a signal for drive from the drive coil Cd to the placement marker Mi/n as shown at Step S112. It is assumed that n=3 in the following.

By transmission of this signal, from the placement markers Mi/3, a signal (for position detection and the like) is sequentially transmitted from the source coil Cm1/3 to Cm3/3 at a timing of the time t1, t2, t3 from the timing of transmission from the drive coil Cd with being sequentially delayed so that they are not overlapped with each other as shown in FIG. 8A to FIG. 8D (S13).

And the sense coils Cx, Cy, Cz in the sense coil unit 43 mounted at the rigid endoscope 21 receive the signal from the respective source coils Cmi/3. And by control of the CPU 70, the sense-coil processing circuit 67 detects the respective three-dimensional positions of the source coils Cmi/3 (placement markers Mi/3)(S14). The three-dimensional positions can be detected (calculated) by detecting the amplitude value and phase of the received signal.

The position information is transmitted to the CPU 70, and the CPU 70 calculates the plane including the three placement markers M1/3 to M3/3 and the coordinate of the center position, for example, of the three placement markers M1/3 to M3/3 from the three placement markers M1/3 to M3/3 (S15).

The CPU 70 may calculate a normal vector perpendicular to the plane from the plane including the placement markers M1/3 to M3/3.

This information is transmitted from the CPU 70 to the video signal processing circuit 75, superimposed on the video signal and outputted to the monitor 24, and the information of the target area is displayed together with the endoscopic image (S16).

Also, the operator 16 reads out the information inputted and stored in the memory 88a and inputted to the CPU 70. This information is also transmitted to the video signal processing circuit 75 from the CPU 70, superimposed on the video signal and outputted to the monitor 24, and displayed on the monitor 24 (S17).

Figure 12:
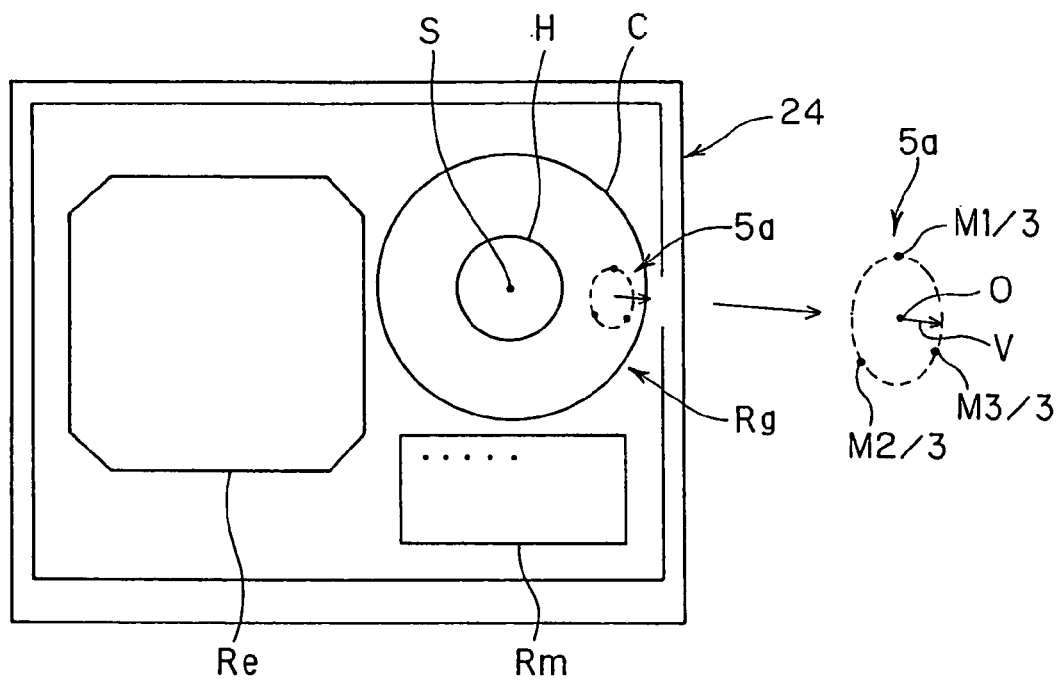
FIG. 12 is a view showing a display example of an endoscopic image and the like on a monitor.

A display example by the monitor 24 is shown in FIG. 12. In a display area Re for the endoscopic image, the endoscopic image captured by the CCD 63 in the rigid endoscope 21 is displayed, while a guide image to be a guide for insertion direction and the like of the tip end side of the insertion portion 40 of the rigid endoscope 21 is displayed in a display area Rg for displaying insertion guide adjacent to this display area Re.

Moreover, in an area Rm for displaying memory storage information, information such as findings by the operator 16 read out of the memory 88a of the placement markers M1/3 to M3/3 is displayed.

In the area Rg for displaying insertion guide in FIG. 12, when the position of the objective lens 62 is set as the origin and the view direction S is set to x' direction, for example, in order that this x' direction is set to a direction perpendicular to the monitor screen and the position of the detected placement marker Mi/n is visually indicated, the position of the placement marker Mi/n is shown using y' and z' components perpendicular to this x' direction at the position displaced by the x' component in the placement marker Mi/n in the view direction S.

That is, the monitor screen relatively shows the y' and z' components of the placement marker Mi/n. In FIG. 12, Mi/n refers to M1/3 to M3/3.

Moreover, since the value of the x' component is hard to be grasped visually in this state, concentric circles H, C with different sizes in proportion to the value of the x' component, for example, are displayed. The sizes of these circles H, C are in proportion to the size of the x' component in the distance from the position P of the tip end portion 40a to the placement marker Mi/n.

For example, the circle C is displayed with the radius of the value of the x' component in the distance from the position P of the tip end portion 40a to the placement marker Mi/n. In such a display, operation to bring the tip end portion 40a closer to the target area 5 side visually is facilitated.

In an example shown in FIG. 12, since the information 5a of the target area 5 is displayed on the right side of the view direction S, the operator 16 can visually and easily grasp the approach to the target area 5 side by changing the tip end portion 40a of the insertion portion 40 to face the right side.

Also, in FIG. 12, the center position of the placement markers M1/3 to M3/3 is displayed as O, and the normal vector V and the like of the plane including them from the center position O of the placement markers M1/3 to M3/3 is displayed. By displaying this normal vector V, it can be determined if the tip end portion 40a is approaching from the direction perpendicular to the plane or from the diagonal direction or the like.

In this way, the operator refers to the information displayed on the monitor 24 and makes an approach to the target area 5 by controlling the orientation of the insertion portion 40 of the rigid endoscope 21 or the like (S18).

In this way, in the insertion guide display area Rg, since the view direction S and the like by the objective lens 62 of the tip end portion 40a of the rigid endoscope 21, the center position O and the like of the target area 5 and the normal vector V and the like of the plane of the target area 5 are displayed, the tip end portion 40a of the insertion portion 40 can be smoothly brought close to the center position O of the target area 5. Also, it can be easily and visually recognized from the normal vector V direction if approach or observation is being made from the direction perpendicular to the plane of the target area 5.

An approach is made to the target area 5, the target area 5 is set in the observation visual field of the objective lens 62 of the rigid endoscope 21, and a treatment is conducted using a treatment instrument, not shown, or the like (S119). Alternatively, the placed placement markers M1/3 to M3/3 are removed. And the surgery is finished.

Supplementary explanation will be given concerning the display and the like of the target area 5 involved in position calculation of the placement markers Mi/3 in FIG. 11.

Suppose that the position of the tip end portion 40a of the rigid endoscope 21 is (xo, yo, zo).

In this case, the position (xo, yo, zo) of the tip end portion 40a of the rigid endoscope 21 and the view direction S of the objective lens 62 is 1) determined in advance from the positions and the respective orientations of the sense coils Cx, Cy, Cz in the sense coil unit 43 mounted to the handle portion 41 and the physical position, direction of the sense coil unit 43 in the state attached to the rigid endoscope 21.

Therefore, if the positions and the respective orientations of the sense coils Cx, Cy, Cz in the sense coil unit 43 are known, the position (xo, yo, zo) of the tip end portion 40a and the view direction S of the objective lens 62 can be determined. And if the result of position calculation of the placement markers Mi/3 is to be displayed on the monitor 24 after the position (xo, yo, zo) of the tip end portion 40a is calculated, by displaying the position of the tip end portion 40a as the origin of the coordinate as mentioned above, visual approach of the tip end portion 40a to the placement markers Mi/3 is facilitated.

In this preferred embodiment, since the sense coil unit 43 is attached to the handle portion 41, the optical system and the like of the rigid endoscope 21 does not interfere with the other parts built in the tip end portion 40a.

In this preferred embodiment, the sense coils Cx, Cy, Cz and the like are detachably mounted to the handle portion 41, but if the sense coil for position detection is provided at the tip end portion 40a of the rigid endoscope 21, it is possible to determine the position of the tip end portion 40a of the rigid endoscope 21 and the view direction S from the position and the orientation of the sense coil. Therefore, the sense coil may be arranged at the tip end portion 40a in this way.

According to this preferred embodiment, by making the relative positional relation between the position of the tip end portion of the endoscope and the marker placed at the target portion of the affected area and the like detectable, the operator can smoothly bring the tip end portion close to the target portion using the information.

Therefore, according to the preferred embodiment, a surgery and the like can be conducted more easily.

In the above-mentioned preferred embodiment, the construction and action has been described that the smooth approach to the target area 5 where the placement markers Mi/n are placed is realized by enabling detection of the position of the tip end portion 40a and the view direction S by the rigid endoscope 21, but it can be also applied to the flexible endoscope 11 as in an example 2 below.

EXAMPLE 2

Figure 13:
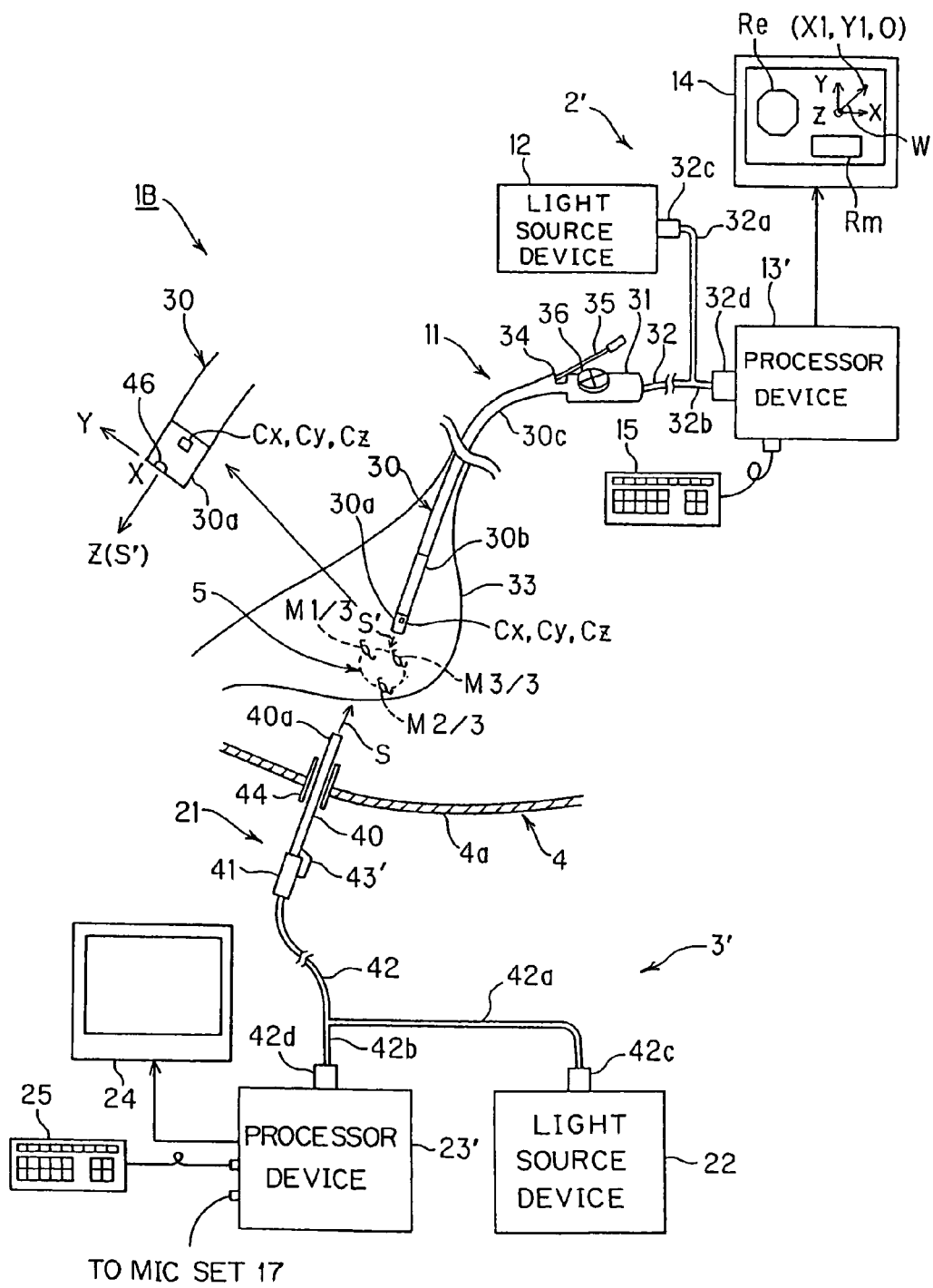
FIG. 13 is a block diagram showing an entire construction of the endoscope system provided with an example 2 of the present invention.

Next, an example 2 of the present invention will be described referring to FIG. 13. FIG. 13 shows an endoscope system 1B provided with the example 2 of the present invention.

In this endoscope system 1B, the sense coils Cx, Cy, Cz are arranged at the tip end portion 30a of the flexible endoscope 11 so that the position of the tip end portion 30a of the flexible endoscope 11 by the sense coils Cx, Cy, Cz and a view direction S' by the objective lens 46 provided at the tip end portion 30a can be detected.

That is, the position of the tip end portion 30a of the insertion portion 30 of the flexible endoscope 11 and the view direction S' of the objective lens 46 are determined from the positions and their orientations of the sense coils Cx, Cy, Cz if the sense coils Cx, Cy, Cz are provided at the tip end portion 30a.

Also, since the image pickup portion in the tip end portion 30a of the flexible endoscope 11 generally comprises a rigid member, the position and the view direction S' of the tip end portion 30a of the flexible endoscope 11 can be determined by incorporating the sense coils Cx, Cy, Cz at the positions displayed rearward by a known position. When the sense coils Cx, Cy, Cz are arranged as above, the optical system such as the objective lens 46 of the flexible endoscope 11 does not interfere with the other parts built in the tip end portion 30a.

On the basis that the above flexible endoscope 11 is used, a case where the placement markers Mi/3 are placed in a living body in advance from the rigid endoscope 21 side will be described.

Assume that the respective space positions of the placement markers M1/3 to M3/3 are (x1, y1, z1), (x2, y2, z2) and (x3, y3, z3).

The view direction S' of the flexible endoscope 11 is set as the Z axis and the origin at the view center of the optical system, and an XYZ space of the coordinate system is set with the upper part in the view as the Y positive direction and the right direction in the view as the X positive direction.

In this coordinate system, a displayed endoscopic image is depicted as a plane perpendicular to the Z axis. The origin of the X, Y, Z is the same as the position of the tip end portion 30a of the above flexible endoscope 11.

The positions (x1, y1, z1), (x2, y2, z2) and (x3, y3, z3) of the placement markers M1/3 to M3/3 detected by the sense coils Cx, Cy, Cz are converted to spatial values of X, Y, Z, respectively.

Their coordinates are (X1, Y1, Z1), (X2, Y2, Z2), (X3, Y3, Z3).

When the tip end portion 30a of the flexible endoscope 11 is assumed to be brought close to the placement marker M1/3, it is equivalent to bringing of the origin of the XYZ space to the coordinate of (X1, Y1, Z1).

Thus, the distance D between the tip end portion and the placement marker M1/3 is a distance between the origin of the X, Y, Z space and the point of (X1, Y1, Z1). In the calculation formula, simple calculation as a square-root of sum of squares of the respective terms of (X1, Y1, Z1) is possible, and this distance can be displayed on the screen.

On the other hand, to which direction to direct the tip end portion 30a of the flexible endoscope 11 to bring the tip end portion 30a of the flexible endoscope 11 closer to the placement marker M1/3 is expressed by the position of the placement marker M1/3 of (X1, Y1, Z1) projected on the XY plane, that is, a vector W from the origin of the X, Y, Z space toward (X1, Y1, 0), since an image is perpendicular to the Z-axis on the endoscopic screen.

By depicting this on the screen, users including operators, who perform endoscopic inspection or treatment, can easily determine to which direction they should direct the tip end of the endoscope.

For example, if X1 and Y1 are both positive, an arrow can be indicated in the diagonally upper right direction, and the placement marker M1/3 exists in that direction. A display example on the monitor 14 corresponding to this case is shown on the display surface of the monitor 14 in FIG. 13.

Also, if X1 and Y1 are both negative, an arrow can be displayed in the diagonally lower left direction, and the placement marker M1/3 exists in that direction.

In this case, too, approach of the tip end portion 30a of the insertion portion 30 to the placement marker M1/3 can be made easily and visually, and a treatment by the flexible endoscope 11 is facilitated. Explanation was given on the case of the placement marker M1/3, but the same applies to the case of the other placement markers M2/3, M3/3.

Alternatively, the vector W shown in the case of the above placement marker M1/3 may be displayed with respect to the center position of the placement markers M1/3 to M3/3.

In FIG. 13, a processor device 13' has the same construction as that of the processor device 23 in FIG. 1, and a processor device 23' has the same construction as that of the processor device 13 in FIG. 1. Moreover, in this case, a unit 43' incorporating a driving coil is connected to the flexible endoscope 21 (corresponding to the driving coil unit 37 in FIG. 1).

FIG. 13 shows a state that, first, a treatment or the like is performed by the rigid endoscope 21, and if a treatment with the flexible endoscope 11 is more preferable, the placement markers M1/3 to M3/3 are placed using grasping forceps and the like, not shown, under observation by the rigid endoscope 11, and then, the tip end portion 30a is made to approach toward the placement markers M1/3 to M3/3 by the flexible endoscope 11.

That is, it corresponds to a case where, in the procedure of the placement of the placement markers M1/3 to M3/3 by the flexible endoscope 11 in the example 1 and the subsequent approach by the rigid endoscope 21 to the target area 5 where the placement markers M1/3 to M3/3 are placed, the functions of the flexible endoscope 11 and the rigid endoscope 21 are switched to each other.

In this way, this preferred embodiment has substantially the same effect as the example 1.

Figure 14:
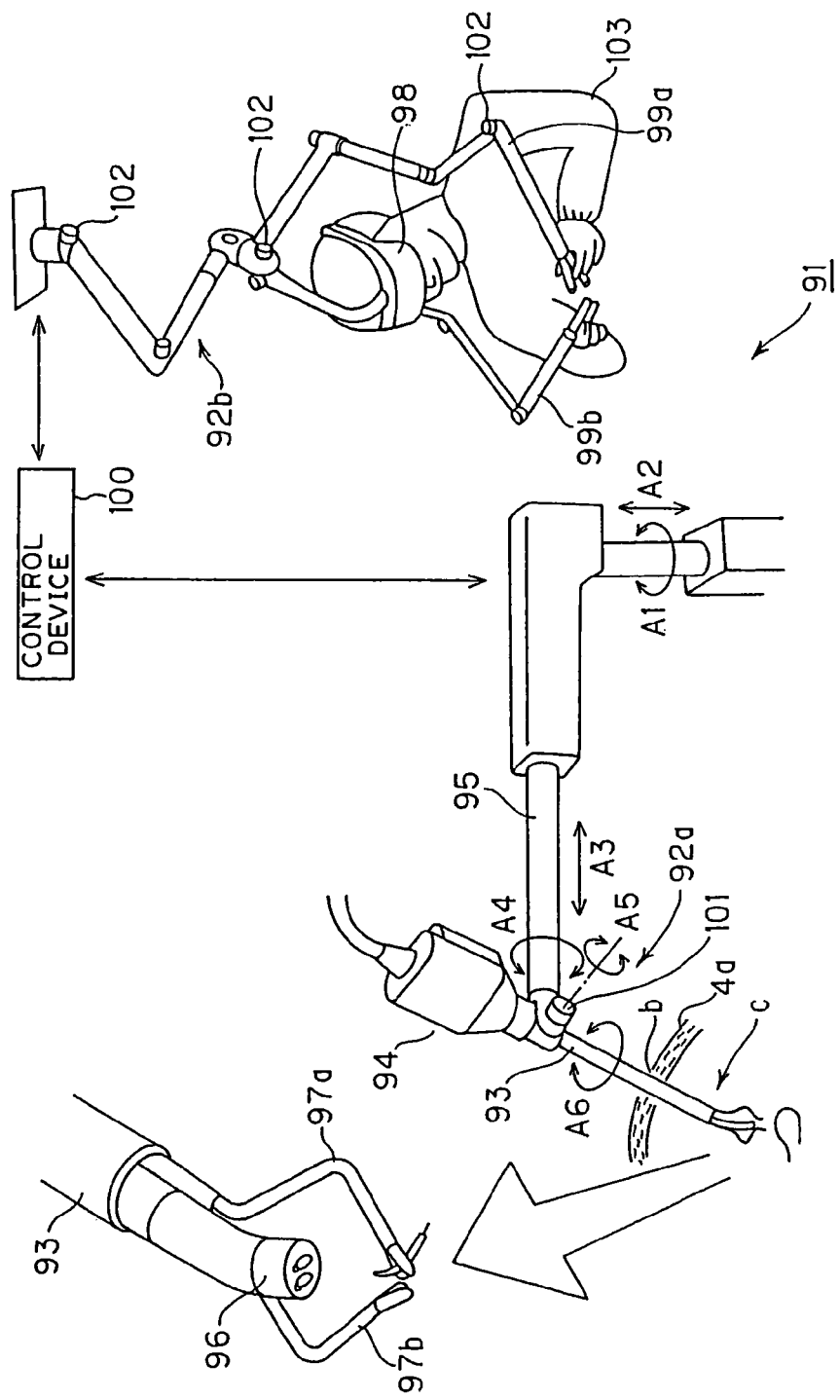
FIG. 14 is a view showing an essential part of an operation system using a manipulator.

The present invention can be also applied to a case where an operation is conducted using manipulators 92a, 92b for operation constituting a robot surgery 91 as shown in FIG. 14. The slave manipulator 92a comprises an operation instrument 94 having an insertion portion 93 with a tip end portion to be inserted into a body c through an insertion hole b into the abdominal portion 4a of a patient and a robot 95 having a plurality of axes with a degree of freedom of straight movement and rotation for supporting this operation instrument 94.

At the tip end portion of the insertion portion 93, a pair of right and left objective optical systems 90a, 90b and a three-dimensional (stereoscopic) scope 96 with image pickup devices, not shown, arranged at the respective image forming positions of the objective optical system 90a, 90b, and a pair of treatment instruments 97a, 97b are provided.

The tip end portion 96a of the stereoscopic scope 96 and the pair of treatment instruments 97a, 97b are capable of being bent with a large degree of freedom.

On the other hand, the master manipulator 92b is provided with a multi-joint structure, and at the tip end portion of this master manipulator 92b, a head mount display (abbreviated as HMD) worn by an operator 103 and a pair of operation arms 99a, 99b for treatment instrument are provided.

The slave manipulator 92a and the master manipulator 92b are connected to a control device 100, and the position of the tip end portion of the master manipulator 92b corresponds to the position of the slave manipulator 92a, and the position of a rotation portion of the HMD 98 corresponds to a bending angle of the three-dimensional scope 96, and further, the operation arms 99a, 99b are controlled by the control device 100 so that they are operated corresponding to the positions of the treatment instruments 97a, 97b.

At the shaft of the slave manipulator 92a, an encoder 101 for detecting an actuator, not shown, and its rotating position and a decelerator, not shown, are provided. Moreover, an encoder 102 is provided at a joint portion of the master manipulator 92b, the rotation portion of the HMD 98 and the joint portions of the operation arms 99a, 99b.

And when the operator 103 operates the master manipulator 92b while observing an image displayed on the HMD 98, the master manipulator 92b generates an operation signal corresponding to the operation and outputs the operation signal to the control device 100.

The control device 100 controls operation of the slave manipulator 92a by this operation signal. By this, when the operator 103 operates the master manipulator 92b while observing an image displayed on the HMD 98, the slave manipulator 92a is operated following the operation so that the operation instrument 94 inserted in the body c can be operated.

Also, the HMD 98 is mounted on the head of the operator 103 and the encoder 102 is mounted at a position to be the rotating shaft of the HMD 98, and when the operator 103 moves the head, following the movement of the encoder 102, the three-dimensional scope 96 fixed to the slave manipulator 92a displays the image in its view on the HMD 98, and the operator 103 can conduct treatment in a realistic sensation as if being in the body c. In FIG. 14, reference characters A1 to A5 denote portions capable of rotation or movement.

In this case, too, if the sense coils Cx, Cy, Cz are provided at the tip end portion 96a of the three-dimensional scope 96, for example, and the placement markers M1/3 to M3/3 are placed at the target areas in the body c, the three-dimensional position in the tip end portion 96a of the three-dimensional scope 96 and its view direction S can be detected, and when they are displayed together with the stereoscopic images and the positions and the like of the placement markers M1/3 to M3/3 on the display surface of the HMD 98, even if the positions of the placement markers M1/3 to M3/3 can not be optically recognized as in the above-mentioned preferred embodiment, the tip end portion 96a of the three-dimensional scope 96 can be easily brought closer to the positions of the placement markers M1/3 to M3/3.

It is to be noted that preferred examples and the like comprising partial combination of the above respective preferred embodiments also belong to the present invention.

What is claimed is:

1. An endoscope system comprising:
   a plurality of markers adapted to be placed at and to define a shape of a target area, each of the plurality of markers being adapted to transmit at least an information for defining the three-dimensional coordinates of the shape of the target area; and
   an endoscope comprising:
      an insertion portion,
      an objective optical system positioned at a tip end portion of the insertion portion, and
      a sensor adapted to detect the information for defining the three-dimensional coordinates of the shape of the target area transmitted by the plurality of markers and to determine the relative positional relation between the insertion portion and the three-dimensional coordinates of the shape of the target area.

2. The endoscope system according to claim 1, wherein the sensor is provided capable of detection of a view direction of the objective optical system.

3. The endoscope according to claim 1, wherein the sensor is detachably mounted to the endoscope.

4. The endoscope system according to claim 1, comprising signal transmitting means for transmitting a driving signal for causing an electromagnetic wave to be transmitted from the marker.

5. The endoscope system according to claim 4, wherein the sensor also functions as the signal transmitting means.

6. The endoscope system according to claim 1, comprising information transmitting means for transmitting a signal for writing information in storage means of the marker.

7. The endoscope system according to claim 6, wherein the sensor also functions as the information transmitting means.

8. The endoscope system according to claim 1, wherein the sensor comprises a plurality of coils for detecting a three-dimensional position.

9. The endoscope system according to claim 1, comprising a control switch for controlling a transmission operation of the marker.

10. The endoscope system according to claim 1, wherein the sensor is provided at the tip end portion of the insertion portion or a grip portion at the base end of the insertion portion.

11. An endoscope comprising:
    an insertion portion;
    an objective optical system positioned at a tip end portion of the insertion portion; and
    a sensor
       adapted to detect information for defining three-dimensional coordinates of a shape of a target area transmitted by a plurality of markers which are adapted to be placed at the target area and to respectively transmit the information of the three-dimensional coordinates for defining the shape of the target area,
       adapted to be positioned to have a predetermined positional relation with the tip end portion of the insertion portion, and
       adapted to determine a relative positional relation between the tip end portion and the three-dimensional coordinates of the shape of the target area.

12. The endoscope according to claim 11, wherein the sensor is provided further capable of detection of a view direction of the objective optical system.

13. The endoscope according to claim 11, wherein the sensor is detachably mounted to the endoscope.

14. The endoscope according to claim 13, wherein with regard to the sensor, a sensor unit incorporating the sensor is detachably mounted to the endoscope.

15. The endoscope according to claim 14, comprising information storing means storing information capable of calculation of a relative positional relation between the position to mount the sensor unit and the tip end portion.

16. The endoscope according to claim 11, comprising signal transmitting means for transmitting a driving signal for causing an electromagnetic wave to be transmitted from the marker.

17. The endoscope according to claim 16, wherein the sensor also functions as the signal transmitting means.

18. The endoscope according to claim 11, comprising information transmitting means for transmitting a signal for writing information in storage means of the marker.

19. The endoscope according to claim 18, wherein the sensor also functions as the information transmitting means.

20. The endoscope according to claim 11, wherein the sensor comprises a plurality of coils for detecting a three-dimensional position.

21. The endoscope according to claim 11, comprising a control switch for controlling a transmission operation of the marker.

22. The endoscope according to claim 11, wherein the sensor is provided at the tip end portion of the insertion portion or at a grip portion the base end of the insertion portion.

23. The endoscope according to claim 11, comprising information storing means for storing information specific to the type of the endoscope.

24. The endoscope according to claim 11, wherein the sensor is connected to position calculating means for calculating a relative positional relation with the marker.

25. An endoscope device comprising:
    a plurality of markers adapted to be placed at and to define a shape of a target area, each of the plurality of markers being adapted to transmit at least an information for defining the three-dimensional coordinates of the shape of the target area; and
    an endoscope comprising:
       an insertion portion,
       an objective optical system positioned at a tip end portion of the insertion portion, and
       a sensor adapted to detect the information for defining the three-dimensional coordinates of the shape of the target area transmitted by the plurality of markers and to determine the relative positional relation between the insertion portion and the three-dimensional coordinates of the shape of the target area; and a signal processing means adapted to calculate a relative positional relation between the position of the plurality of markers and the tip end portion by the output signal of the sensor and for outputting information on the calculated positional relation to display means.

26. The endoscope device according to claim 25, wherein the signal processing means further performs signal processing for calculating a view direction of the objective optical system.

27. The endoscope device according to claim 25, further comprising display means for displaying information on the positional relation and the view direction of the objective optical system.

28. The endoscope device according to claim 25, wherein the display means displays an endoscopic image captured by image pickup means provided at the endoscope.

29. The endoscope device according to claim 25, wherein the display means has a display portion for displaying information read out of storage means provided at the marker.

30. The endoscope device according to claim 25, wherein the signal processing means has marker position calculating means for calculating the position of the marker based on the output signal of the sensor.

31. The endoscope device according to claim 25, wherein the display means displays a relative positional relation between the tip end portion and the marker.

32. The endoscope device according to claim 25, wherein the display means displays guide information including moving direction to bring the tip end portion close to the position of the plurality of markers.

33. The endoscope device according to claim 25, wherein the signal processing means has a write signal generating means for generating a signal to write information in storage means provided at the marker.

34. The endoscope device according to claim 33, wherein the write signal generating means generates a signal to write in the storage means from an input signal by a keyboard or a voice input signal from a microphone.

35. The endoscope device according to claim 25, wherein with regard to the sensor, a sensor unit incorporating the sensor is detachably mounted to the endoscope.

36. The endoscope device according to claim 25, wherein the endoscope is a rigid endoscope with the insertion portion which is rigid.

37. The endoscope device according to claim 25, wherein the endoscope is a flexible endoscope with the insertion portion which is flexible.

38. The endoscope device according to claim 25, wherein the endoscope is a stereoscopic scope provided with a pair of objective optical systems.

39. The endoscope device according to claim 38, further comprising a control device for controlling movement of the stereoscopic scope according to an operation signal.

40. The endoscope device according to claim 39, comprising an operation signal generating means for generating the operation signal to the control device.

41. A guide aiding method for bringing a tip end portion of an endoscope close to a target area, comprising steps of:
   placing a plurality of placement markers which generate electromagnetic waves to define a shape of a target area in advance;
   signal transmitting start processing for processing of transmitting a signal to the plurality of placement markers;
   position calculation processing for calculation processing of a three-dimensional position of the plurality of placement markers by receiving the signal from the plurality of placement markers by a sensor provided in the endoscope; and
   information display processing for processing to display information on positional relation between the tip end portion of the endoscope and the position of the plurality of placement markers.

42. The guide aiding method according to claim 41, further comprising a step of storage information display processing for processing display of information stored in a storage means provided at the placement marker.

* * * * *